United States Patent
LaRose et al.

(10) Patent No.: US 9,050,405 B2
(45) Date of Patent: *Jun. 9, 2015

(54) STABILIZING DRIVE FOR CONTACTLESS ROTARY BLOOD PUMP IMPELLER

(71) Applicant: HeartWare, Inc., Miami Lakes, FL (US)

(72) Inventors: Jeffrey A. LaRose, Parkland, FL (US); Charles R. Shambaugh, Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/191,312

(22) Filed: Feb. 26, 2014

(65) Prior Publication Data

US 2014/0179983 A1 Jun. 26, 2014

Related U.S. Application Data

(63) Continuation of application No. 13/181,240, filed on Jul. 12, 2011, now Pat. No. 8,672,611, which is a continuation-in-part of application No. 11/654,226, filed on Jan. 16, 2007, now Pat. No. 7,976,271.

(Continued)

(51) Int. Cl.
*F04D 29/048* (2006.01)
*F01D 3/00* (2006.01)
(Continued)

(52) U.S. Cl.
CPC ............ *A61M 1/1036* (2014.02); *A61M 1/101* (2013.01); *F04D 13/0666* (2013.01);
(Continued)

(58) Field of Classification Search
CPC ... A61M 1/10; A61M 1/1015; A61M 1/1031; A61M 1/1036; A61M 1/101; A61M 1/1017; F04D 29/048; F04D 29/047; F04D 13/0633
USPC .............. 415/104, 900; 416/144, 223 B, 500; 417/420
See application file for complete search history.

(56) References Cited

U.S. PATENT DOCUMENTS 2,362,667 A 11/1944 Schmidt
3,142,519 A 7/1964 Abramovitz
(Continued)

FOREIGN PATENT DOCUMENTS

JP 2000-188822 A 7/2000
JP 2002-541986 12/2002
WO WO 00/64509 11/2000

OTHER PUBLICATIONS

International Preliminary Report on Patentability issued by the International Bureau of WIPO in connection with International Application No. PCT/US2007/000763.

(Continued)

*Primary Examiner* — Dwayne J White
*Assistant Examiner* — Ryan Ellis
(74) *Attorney, Agent, or Firm* — Lerner, David, Littenberg, Krumholz & Mentlik, LLP

(57) ABSTRACT

A rotary blood pump includes a casing defining a pumping chamber. The pumping chamber has a blood inlet and a tangential blood outlet. One or more motor stators are provided outside of the pumping chamber. A rotatable impeller is within the pumping chamber and is adapted to cause blood entering the pumping chamber to move to the blood outlet. The impeller has one or more magnetic regions. The impeller is radially constrained in rotation by magnetic coupling to one or more motor stators and is axially constrained in rotation by one or more hydrodynamic thrust bearing surfaces on the impeller.

21 Claims, 11 Drawing Sheets

Related U.S. Application Data

(60) Provisional application No. 60/758,794, filed on Jan. 13, 2006, provisional application No. 60/758,892, filed on Jan. 13, 2006, provisional application No. 60/758,793, filed on Jan. 13, 2006, provisional application No. 60/758,795, filed on Jan. 13, 2006.

(51) Int. Cl.
  *A61M 1/10* (2006.01)
  *F04D 13/06* (2006.01)
  *A61M 1/12* (2006.01)
  *F04D 29/047* (2006.01)

(52) U.S. Cl.
  CPC ......... *F04D 29/048* (2013.01); *F04D 13/0633* (2013.01); *A61M 1/1015* (2014.02); *A61M 1/1017* (2014.02); *A61M 1/1031* (2014.02); *A61M 1/122* (2014.02); *A61M 1/1029* (2014.02); *F04D 29/0473* (2013.01)

(56) References Cited

U.S. PATENT DOCUMENTS

| | | | |
|---|---|---|---|
| 3,608,088 A | 9/1971 | Dorman et al. | |
| 4,004,298 A | 1/1977 | Freed | |
| 4,606,698 A | 8/1986 | Clausen et al. | |
| 4,625,712 A | 12/1986 | Wampler | |
| 4,642,036 A | 2/1987 | Young | |
| 4,688,998 A | 8/1987 | Olsen et al. | |
| 4,704,121 A | 11/1987 | Moise | |
| 4,745,345 A | 5/1988 | Petersen | |
| 4,753,221 A | 6/1988 | Kensey et al. | |
| 4,763,032 A | 8/1988 | Bramm et al. | |
| 4,769,031 A | 9/1988 | McGough et al. | |
| 4,779,614 A | 10/1988 | Moise | |
| 4,806,080 A | 2/1989 | Mizobuchi et al. | |
| 4,817,586 A | 4/1989 | Wampler | |
| 4,846,152 A | 7/1989 | Wampler et al. | |
| 4,880,362 A | 11/1989 | Laing et al. | |
| 4,895,557 A | 1/1990 | Moise et al. | |
| 4,906,229 A | 3/1990 | Wampler | |
| 4,908,012 A | 3/1990 | Moise et al. | |
| 4,919,647 A | 4/1990 | Nash | |
| 4,944,722 A | 7/1990 | Carriker et al. | |
| 4,944,748 A | 7/1990 | Bramm et al. | |
| 4,957,504 A | 9/1990 | Chardack | |
| 4,994,017 A | 2/1991 | Yozu | |
| 4,994,078 A | 2/1991 | Jarvik | |
| 5,017,103 A | 5/1991 | Dahl | |
| 5,049,134 A | 9/1991 | Golding et al. | |
| 5,055,005 A | 10/1991 | Kletschka | |
| 5,078,741 A | 1/1992 | Bramm et al. | |
| 5,079,467 A | 1/1992 | Dorman | |
| 5,092,844 A | 3/1992 | Schwartz et al. | |
| 5,106,263 A | 4/1992 | Irie | |
| 5,112,200 A | 5/1992 | Isaacson et al. | |
| 5,112,202 A | 5/1992 | Oshima et al. | |
| 5,129,789 A | 7/1992 | Thornton et al. | |
| 5,145,333 A | 9/1992 | Smith | |
| 5,147,187 A | 9/1992 | Ito et al. | |
| 5,147,388 A | 9/1992 | Yamazaki | |
| 5,149,253 A | 9/1992 | Miyamoto et al. | |
| 5,158,440 A | 10/1992 | Cooper et al. | |
| 5,160,246 A | 11/1992 | Horiuchi | |
| 5,182,533 A | 1/1993 | Ritts | |
| 5,195,877 A | 3/1993 | Kletschka | |
| 5,205,721 A | 4/1993 | Isaacson | |
| 5,211,546 A | 5/1993 | Isaacson et al. | |
| 5,290,236 A | 3/1994 | Mathewson | |
| 5,302,091 A * | 4/1994 | Horiuchi | 417/420 |
| 5,324,177 A | 6/1994 | Golding et al. | |
| 5,368,438 A | 11/1994 | Raible | |
| 5,370,509 A | 12/1994 | Golding et al. | |
| 5,376,114 A | 12/1994 | Jarvik | |
| 5,385,409 A | 1/1995 | Ide | |
| 5,393,207 A | 2/1995 | Maher et al. | |
| 5,399,145 A | 3/1995 | Ito et al. | |
| 5,405,251 A | 4/1995 | Sipin | |
| 5,443,503 A | 8/1995 | Yamane | |
| 5,470,208 A | 11/1995 | Kletschka | |
| 5,501,574 A | 3/1996 | Raible | |
| 5,507,629 A | 4/1996 | Jarvik | |
| 5,542,817 A * | 8/1996 | Brandt | 415/58.2 |
| 5,575,630 A | 11/1996 | Nakazawa et al. | |
| 5,591,017 A | 1/1997 | Dwyer | |
| 5,601,418 A | 2/1997 | Ohara et al. | |
| 5,613,935 A | 3/1997 | Jarvik | |
| 5,649,811 A | 7/1997 | Krol, Jr. et al. | |
| 5,658,136 A | 8/1997 | Mendler | |
| 5,676,035 A | 10/1997 | Chrestoff et al. | |
| 5,692,882 A | 12/1997 | Bozeman, Jr. et al. | |
| 5,711,753 A | 1/1998 | Pacella et al. | |
| 5,713,730 A | 2/1998 | Nose et al. | |
| 5,722,930 A | 3/1998 | Larson, Jr. et al. | |
| 5,725,357 A | 3/1998 | Nakazeki et al. | |
| 5,746,575 A | 5/1998 | Westphal et al. | |
| 5,749,855 A | 5/1998 | Reitan | |
| 5,755,784 A | 5/1998 | Jarvik | |
| 5,776,190 A | 7/1998 | Jarvik | |
| 5,803,720 A * | 9/1998 | Ohara et al. | 417/420 |
| 5,810,479 A | 9/1998 | Miyasaka et al. | |
| 5,810,708 A | 9/1998 | Woodard et al. | |
| 5,824,070 A | 10/1998 | Jarvik | |
| 5,829,338 A | 11/1998 | Chrestoff et al. | |
| 5,840,070 A | 11/1998 | Wampler | |
| 5,863,179 A | 1/1999 | Westphal et al. | |
| 5,888,241 A | 3/1999 | Jarvik | |
| 5,904,646 A | 5/1999 | Jarvik | |
| 5,924,848 A | 7/1999 | Izraelev | |
| 5,924,975 A | 7/1999 | Goldowsky | |
| 5,928,131 A | 7/1999 | Prem | |
| 5,938,412 A | 8/1999 | Izraelev | |
| 5,947,892 A | 9/1999 | Benkowski et al. | |
| 5,951,169 A | 9/1999 | Oklejas | |
| 6,001,056 A | 12/1999 | Jassawalla et al. | |
| 6,007,478 A | 12/1999 | Siess et al. | |
| 6,015,272 A | 1/2000 | Antaki et al. | |
| 6,015,434 A | 1/2000 | Yamane | |
| 6,030,188 A | 2/2000 | Nojiri et al. | |
| 6,036,435 A | 3/2000 | Oklejas | |
| 6,042,347 A | 3/2000 | Scholl et al. | |
| 6,058,593 A | 5/2000 | Siess | |
| 6,071,093 A | 6/2000 | Hart | |
| 6,074,180 A | 6/2000 | Khanwilkar et al. | |
| 6,080,133 A | 6/2000 | Wampler | |
| 6,111,332 A | 8/2000 | Post | |
| 6,118,199 A | 9/2000 | Lembke | |
| 6,120,537 A | 9/2000 | Wampler | |
| 6,132,094 A | 10/2000 | Cornelison et al. | |
| 6,135,710 A | 10/2000 | Araki et al. | |
| 6,139,487 A | 10/2000 | Siess | |
| 6,152,704 A | 11/2000 | Aboul-Hosn et al. | |
| 6,155,969 A | 12/2000 | Schima et al. | |
| 6,171,078 B1 | 1/2001 | Schob | |
| 6,176,822 B1 | 1/2001 | Nix et al. | |
| 6,176,848 B1 | 1/2001 | Rau et al. | |
| 6,183,220 B1 | 2/2001 | Ohara et al. | |
| 6,200,260 B1 | 3/2001 | Bolling | |
| 6,206,659 B1 | 3/2001 | Izraelev | |
| 6,227,797 B1 | 5/2001 | Watterson et al. | |
| 6,227,817 B1 | 5/2001 | Paden | |
| 6,227,820 B1 | 5/2001 | Jarvik | |
| 6,234,772 B1 | 5/2001 | Wampler | |
| 6,234,998 B1 | 5/2001 | Wampler | |
| 6,244,835 B1 | 6/2001 | Antaki et al. | |
| 6,250,230 B1 | 6/2001 | Post | |
| 6,250,880 B1 | 6/2001 | Woodard et al. | |
| 6,304,015 B1 | 10/2001 | Filatov et al. | |
| 6,346,071 B1 | 2/2002 | Mussivand | |
| 6,387,037 B1 | 5/2002 | Bolling et al. | |
| 6,390,969 B1 | 5/2002 | Bolling et al. | |
| 6,439,845 B1 | 8/2002 | Veres | |
| 6,447,266 B2 | 9/2002 | Antaki et al. | |

(56) References Cited

U.S. PATENT DOCUMENTS

| | | | |
|---|---|---|---|
| 6,527,699 | B1 | 3/2003 | Goldowsky |
| 6,530,876 | B1 | 3/2003 | Spence |
| 6,544,216 | B1 | 4/2003 | Sammler et al. |
| 6,547,539 | B2 | 4/2003 | Izraelev |
| 6,589,031 | B2 | 7/2003 | Maeda et al. |
| 6,595,762 | B2 | 7/2003 | Khanwilkar et al. |
| 6,609,883 | B2 | 8/2003 | Woodard et al. |
| 6,610,004 | B2 | 8/2003 | Viole et al. |
| 6,623,475 | B1 | 9/2003 | Siess |
| 6,638,011 | B2 | 10/2003 | Woodard et al. |
| 6,641,378 | B2 | 11/2003 | Davis et al. |
| 6,688,861 | B2 * | 2/2004 | Wampler ............ 417/423.7 |
| 6,716,189 | B1 | 4/2004 | Jarvik |
| 6,722,863 | B2 | 4/2004 | Maeda et al. |
| 6,846,168 | B2 | 1/2005 | Davis et al. |
| 6,879,074 | B2 | 4/2005 | Amrhein et al. |
| 6,884,210 | B2 | 4/2005 | Nose et al. |
| 6,966,748 | B2 | 11/2005 | Woodard et al. |
| 6,981,942 | B2 | 1/2006 | Khaw et al. |
| 7,021,905 | B2 | 4/2006 | Torrey et al. |
| 7,156,873 | B2 | 1/2007 | Nose et al. |
| 7,281,896 | B2 * | 10/2007 | Yu et al. ............ 416/144 |
| 7,416,525 | B2 | 8/2008 | Wampler et al. |
| 7,431,688 | B2 | 10/2008 | Wampler et al. |
| 7,470,246 | B2 | 12/2008 | Mori et al. |
| 7,476,077 | B2 | 1/2009 | Woodard et al. |
| 7,682,301 | B2 | 3/2010 | Wampler et al. |
| 7,748,964 | B2 | 7/2010 | Yaegashi et al. |
| 7,753,645 | B2 | 7/2010 | Wampler et al. |
| 7,802,966 | B2 | 9/2010 | Wampler et al. |
| 7,976,271 | B2 * | 7/2011 | LaRose et al. ............ 415/104 |
| 7,997,854 | B2 | 8/2011 | LaRose et al. |
| 8,672,611 | B2 * | 3/2014 | LaRose et al. ............ 415/104 |
| 2003/0113208 | A1 | 6/2003 | Hart et al. |
| 2003/0233021 | A1 | 12/2003 | Nose et al. |
| 2004/0143151 | A1 | 7/2004 | Mori et al. |
| 2004/0228724 | A1 | 11/2004 | Capone et al. |
| 2004/0236420 | A1 | 11/2004 | Yamane et al. |
| 2004/0241019 | A1 | 12/2004 | Goldowsky |
| 2005/0025630 | A1 | 2/2005 | Ayre et al. |
| 2005/0084398 | A1 | 4/2005 | Wampler et al. |
| 2005/0107657 | A1 | 5/2005 | Carrier et al. |
| 2005/0250975 | A1 | 11/2005 | Carrier et al. |
| 2005/0254976 | A1 | 11/2005 | Carrier et al. |
| 2006/0083642 | A1 | 4/2006 | Cook |
| 2007/0078293 | A1 | 4/2007 | Shambaugh et al. |
| 2007/0280841 | A1 | 12/2007 | LaRose et al. |
| 2008/0080983 | A1 | 4/2008 | Wampler et al. |
| 2008/0089797 | A1 | 4/2008 | Wampler et al. |
| 2008/0095648 | A1 | 4/2008 | Wampler et al. |
| 2012/0035411 | A1 | 2/2012 | LaRose et al. |

OTHER PUBLICATIONS

Written Opinion of the International Searching Authority issued by the International Searching Authority (ISA/US) in connection with International Application No. PCT/US2007/000763.
Office Action issued Sep. 26, 2008 in connection with U.S. Appl. No. 11/654,216, filed Jan. 16, 2007.
Final Office Action issued May 28, 2009 in connetion with U.S. Appl. No. 11/654,216, filed Jan. 16, 2007.
Advisory Action issued Aug. 25, 2009 in connection with U.S. Appl. No. 11/654,216, filed Jan. 16, 2007.
Office Action issued Dec. 18, 2009 in connection with U.S. Appl. No. 11/654,216, filed Jan. 16, 2007.
First Official Action, issued Dec. 18, 2009, in connection with Chinese Patent Application No. 200780003014.7 with English translation.
International Search Report issued Nov. 5, 2007 by the International Searching Authority (ISA/US) in connection with International Application No. PCT/US2007/000763.
Final Office Action issued Aug. 16, 2010 in connection with U.S. Appl. No. 11/654,216, filed Jan. 16, 2007.
Office Action issued Aug. 5, 2009 in connection with U.S. Appl. No. 11/654,217, filed Jan. 16, 2007.
Final Office Action issued Feb. 23, 2010 in connection with U.S. Appl. No. 11/654,217, filed Jan. 16, 2007.
Office Action issued Jun. 21, 2010 in connection with U.S. Appl. No. 11/654,217, filed Jan. 16, 2007.
Notice of Allowance issued Oct. 27, 2010 in connection with U.S. Appl. No. 11/654,217, filed Jan. 16, 2007.
Notice of Allowance issued Feb. 14, 2011 in connection with U.S. Appl. No. 11/654,217, filed Jan. 16, 2007.
Notice of Allowance issued Apr. 14, 2011 in connection with U.S. Appl. No. 11/654,217, filed Jan. 16, 2007.
Issue Notification issued Jul. 27, 2011 in connection with U.S. Appl. No. 11/654,217, filed Jan. 16, 2007.
Office Action issued Sep. 23, 2009 in connection with U.S. Appl. No. 11/654,226, filed Jan. 16, 2007.
Final Office Action issued Jul. 21, 2010 in connection with U.S. Appl. No. 11/654,226, filed Jan. 16, 2007.
Notice of Allowance issued Nov. 16, 2010 in connection with U.S. Appl. No. 11/654,226, filed Jan. 16, 2007.
Notice of Allowance issued Mar. 2, 2011 in connection with U.S. Appl. No. 11/654,226, filed Jan. 16, 2007.
Office Action issued Jun. 21, 2011 in connection with U.S. Appl. No. 11/654,216, filed Jan. 16, 2007.
Notice of Allowance issued Apr. 9, 2012 in connection with U.S. Appl. No. 11/654,216, filed Jan. 16, 2007.
Office Action issued Nov. 22, 2011 in connection with Japanese Patent Application No. 2008-550412, filed Jan. 12, 2007.
Examiner's First Report issued Aug. 11, 2011 in connection with Australian Patent Application No. 2007207782, filed Jul. 18, 2008.
First Office Action issued Dec. 18, 2009 in connection with Chinese Patent Application No. 200780003014.7, filed Jan. 12, 2007.
Second Office Action issued Mar. 5, 2012 in connection with Chinese Patent Application No. 200780003014.7, filed Jan. 12, 2007.
Issue Notification issued Jun. 22, 2011 in connection with U.S. Appl. No. 11/654,226, filed Jan. 16, 2007.
Office Action issued Feb. 12, 2012 in connection with U.S. Appl. No. 13/181,240, filed Jul. 12, 2011.
Response to Office Action issued Feb. 12, 2012, filed Jun. 11, 2013 in connection with U.S. Appl. No. 13/181,240, filed Jul. 12, 2011.
Office Action issued Jul. 2, 2013 in connection with U.S. Appl. No. 13/181,240, filed Jul. 12, 2011.
Response to Office Action issued Jul. 2, 2013, filed Oct. 2, 2013, in connection with U.S. Appl. No. 13/181,240, filed Jul. 12, 2011.
Notice of Allowance issued Oct. 28, 2013 in connection with U.S. Appl. No. 13/181,240, filed Jul. 12, 2011.

* cited by examiner

STABILIZING DRIVE FOR CONTACTLESS ROTARY BLOOD PUMP IMPELLER

This application is a continuation of U.S. Ser. No. 13/181,240, filed Jul. 12, 2011, now allowed, which is a continuation-in-part of U.S. Ser. No. 11/654,226, filed Jan. 16, 2007, now U.S. Pat. No. 7,976,271, issued Jul. 12, 2011, which claims the benefit of U.S. Provisional Applications Nos. 60/758,793, filed Jan. 13, 2006; 60/758,892, filed Jan. 13, 2006; 60/758,795, filed Jan. 13, 2006; and 60/758,794, filed Jan. 13, 2006, the entire contents of each of which is hereby incorporated by reference in its entirety into this application.

FIELD OF THE INVENTION

The present invention relates to rotary pumps and, more specifically, to centrifugal rotary blood pumps and methods of therapeutic support utilizing such pumps, in which an impeller within the pump rotates on wearless hydrodynamic and magnetic bearings which permit blood to be moved from a pump inlet to a pump outlet by the impeller in contact only with the volume of blood within the pump.

BACKGROUND OF THE INVENTION

Clinical applications of ventricular assist devices to support patients with end-stage heart disease, as a bridge to cardiac transplantation, or as an end stage therapeutic modality have become an accepted clinical practice in cardiovascular medicine. It is estimated that greater than 35,000 persons suffering from end stage cardiac failure are candidates for cardiac support therapy.

Ventricular assist devices may utilize a blood pump for imparting momentum to a patient's blood thereby driving the blood to a higher pressure. One example of a ventricular assist device is a Left Ventricular Assist Device (LVAD). The LVAD is attached to the left ventricle of the patient's heart where oxygenated blood enters the LVAD through a blood inlet of the LVAD. The LVAD then imparts momentum to the blood. By connecting a blood outlet of the LVAD to the patient's aorta, pumped blood may reenter the patient's circulatory system.

Ventricular assist devices, such as the LVAD, have heretofore utilized positive displacement pumps and rotary pumps. Positive displacement pumps force blood from a first chamber to a second chamber by reducing the volume of the first chamber while increasing the volume of the second chamber to draw blood into the chamber. Such pumps are normally provided with check valves that only permit flow in one direction and are normally large and prone to mechanical wear. The human heart is a natural example of a positive displacement pump. A rotary pump forces blood by the spinning of an impeller within the pump. Known types of pumps utilize an impeller to impart momentum to the blood through the use of propeller type impeller blades which push the blood.

Rotary blood pumps may be either centrifugal or axial. In a centrifugal blood pump, blood enters the pump along its axis of rotation and exits the pump perpendicular to the axis of rotation. In an axial blood pump, blood enters the pump along its axis of rotation and exits the pump along the axis of rotation.

Traditionally, rotary blood pumps include a rotor consisting of a shaft and an impeller coupled to the shaft. Mechanical bearings are used to stabilize the rotor, both axially and radially, so the impeller could remain free to rotate smoothly while being constrained in the axial and radial directions. Mechanical bearings within the volume of blood have become the source of thrombosis. Moreover, as the use of mechanical bearings necessitated the protrusion of the shaft beyond the pumping chamber, a seal was required to prevent the escape of blood from the pumping chamber. This too became a source of thrombosis and sometimes hemolysis, as well as premature wear.

The use of seals for mechanical shafts in rotary blood pumps has been shown to be suboptimal as seals could cause thrombosis of the blood and could wear out prematurely. To minimize the risk of thrombosis and failed seals, sealless rotary blood pumps have been developed. For example, U.S. Pat. No. 5,695,471 to Wampler and U.S. Pat. No. 6,846,168 to Davis et al. (the '168 patent), both herein incorporated by reference, relate to sealless rotary blood pumps. In such sealless rotary blood pumps, the rotor and/or impeller may be suspended within the pumping chamber by the use of magnetic and/or fluid forces.

Magnetic and/or fluid forces used to suspend the impeller within the pumping chamber could serve to stabilize the impeller, allowing for rotation while preventing excessive axial or radial movement. Wearless stabilization of an impeller can be achieved by magnetic bearings and hydrodynamic bearings. In this way, magnetic forces form magnetic bearings and fluid forces form hydrodynamic bearings.

Several forms of magnetic bearings have been developed. In one form, passive magnetic bearings in the form of permanent magnets can be embedded in both the rotor and the pump housing to provide magnetic coupling that may keep the impeller suspended in position within the pump casing. Such permanent magnets embedded in both the rotor and the pump casing provide repulsive forces that may keep the impeller suspended within the pump casing. Such magnetic bearings are said to be passive magnetic bearings as no control is used to keep the impeller properly centered. While passive magnetic bearings may be effective at keeping the impeller suspended in one direction, for example in the radial direction, it has been shown that such passive magnetic bearings alone cannot keep an impeller suspended in both the axial and radial directions.

Active magnetic bearings in the form of electromagnets can be used, for example in or on the pump housing, magnetically to couple with and to drive the impeller. Power to the electromagnets may then be varied, as required, to adjust the magnetic field in response to displacement so that the impeller may be kept in position.

Electromagnets may also be used, for example, in the pump casing, to provide the repulsive magnetic force. These bearings are said to be active magnetic bearings as the magnetic fields are actively controlled to maintain proper impeller position.

Because of the complexity of active magnetic bearings, rotary blood pumps have been developed to use both passive magnetic bearings and hydrodynamic bearings to suspend the impeller in a sealless rotary blood pump. For example, U.S. Pat. No. 6,234,772, to Wampler et al. (the '772 patent), herein incorporated by reference, relates to a sealless rotary blood pump with passive magnetic bearings and hydrodynamic bearings. In the '772 patent, radial suspension is enabled by a series of magnetic discs within the impeller shaft and corresponding series of magnetic rings in the pump casing. In the '168 patent, radial suspension is enabled by a series of magnetic rings within a spindle that protrudes through a hole in the center of the impeller. A corresponding series of magnetic discs is provided within the impeller whereby the impeller is suspended about the spindle during rotation. In the '772 patent, axial suspension is enabled by a set of hydrodynamic thrust bearing surfaces on the impeller.

There remains a need for smaller and more efficient rotary blood pumps. In particular, there remains a need for wearless centrifugal pumps with hydrodynamic bearings and improved continuous fluid flow paths within the pump to further diminish the risks of hemolysis and thrombosis in the blood being pumped. By developing more sophisticated rotary blood pump impellers with hydrodynamic bearings and passive magnetic bearings, the physical size, performance and efficiency of the rotary blood pump may be improved to the point where consistent and reliable therapeutic support may be provided.

BRIEF SUMMARY OF THE INVENTION

A centrifugal rotary blood pump for implantation within the pericardial space includes a housing defining a pumping chamber with upper and lower interior surfaces. The pumping chamber has a blood inlet and a blood outlet. A rotatable impeller is within the pumping chamber and is adapted to increase blood pressure within the pumping chamber when rotating to cause blood to move to the blood outlet. The impeller has a hollow interior space containing spaced apart sets of interior wall surface areas. Each of the sets of interior wall surface areas consists of a plurality of wall surface areas each substantially perpendicular to the other. At least one of the interior wall surface areas has at least one bore closed at one end. The longitudinal axis of the bore extends in one direction relative to the direction of rotation of the impeller.

In an embodiment, the longitudinal axis of the bore extends substantially parallel to the rotational axis of the impeller.

In another embodiment, the longitudinal axis of the bore extends substantially perpendicular to the rotational axis of the impeller.

In another embodiment, the longitudinal axis of the bore extends substantially parallel to the direction of rotation of the impeller.

In another embodiment, each of the sets of interior wall surface areas has a bore.

In another embodiment, each of the sets of interior wall surface areas has a plurality of side-by-side bores extending in one direction relative to the direction of rotation of the impeller.

In another embodiment, at least one of the interior wall surface areas of each of the sets of wall surface areas has at least one bore closed at one end, the longitudinal axis of the bore extending in one direction relative to the rotational axis of the impeller.

In another embodiment, each of the interior wall surface areas of each of the sets of wall surface areas has at least one bore closed at one end, the longitudinal axis of at least one bore extending in one direction relative to the rotational axis of the impeller.

In another embodiment, each of the spaced apart sets of interior wall surface areas is oriented diagonally across the impeller from another of the sets of interior wall surface areas.

A centrifugal rotary blood pump for implantation within the pericardial space includes a housing defining a pumping chamber. The pumping chamber has an axial blood inlet and a tangential volute defining a blood outlet. One or more magnetic motor stators are provided outside of the pumping chamber. A rotatable impeller is within the pumping chamber and is adapted to pressurize blood entering the pumping chamber for exiting at the blood outlet. The impeller has one or more magnetic regions. The impeller is radially and axially suspended in rotation by magnetic forces created by passive and active sources of magnetic flux acting upon the impeller and one or more hydrodynamic thrust bearings provided on an upper surface of the impeller. The housing assembly may have an upper or front casing and a rear or lower casing which, when assembled, form a substantially cylindrical pumping chamber and a volute having a tangential blood outflow port. In one embodiment, when assembled, the housing defines a substantially cylindrical pumping chamber. A relatively short inflow cannula is integrated with the upper casing and is adapted for insertion into a ventricle of the heart. The outflow port is directed perpendicular to the axis of the inflow cannula. The blood inflow cannula may be straight, curved or otherwise bent to facilitate the fit of the blood pump into the thoracic cavity of the patient or to improve blood flow characteristics.

An electromagnetic motor for driving the pump consists of fixed electromagnetic stator portions outside the blood flow region and the adjacent rotatable impeller within the pumping chamber adapted to create fluid pressure within the pumping chamber so that blood moves from the inflow to the outflow port. In one embodiment, the motor is a dual stator axial flux gap design with the impeller located within the pumping chamber between spaced apart motor stators. An upper motor stator is located adjacent or on the upper or front casing and a lower motor stator is located adjacent the lower or rear casing. Each motor stator contains a plurality of electrical coils or windings arranged on a substantially circular iron core member for efficient electromagnetic coupling with corresponding magnetic regions of the impeller to cause the impeller to rotate within the pumping chamber. The upper motor stator may be positioned closer to the impeller than the lower motor stator to impose an axial magnetic preload on the impeller to counter the magnetic impact on the impeller of the lower motor stator. In some situations a single stator is placed on or adjacent the upper casing for the same purpose. In one embodiment, each motor stator is co-axial with the rotational axis of the impeller. The impeller and each motor stator are essentially circular in horizontal cross section and may have substantially the same diameter to aid in radial stiffness of the rotating impeller during operation of the pump. Electrical power is delivered to the coil windings by a plurality of power cables carried within an elongated pliable cylinder. In one embodiment the pliable cylinder is made from silicone and may have a urethane sheath. The pliable cylinder has a plurality of lumens therein, each of which carries a power cable. In one embodiment there are six such lumens.

The impeller has a substantially circular circumference and may be formed from a ferromagnetic substance. Ferromagnetic substances may be materials that are strictly ferromagnetic as well as materials that are ferrimagnetic. A suitable ferromagnetic substance may be, for example, compression bonded neodymium or Alnico (aluminum-nickel alloy). A ferromagnetic impeller allows for the magnetization of various regions of the impeller in a desired configuration. A ferromagnetic impeller may be treated with a conformal, protective polymer coating of an organic polymer such as Parylene, or silicone, to prevent oxidation by forming a hermetic seal around the rotor. On top of this, a hard, lubricious protective coating may be applied over the conformal polymer coating, to protect against wear and abrasion. Such coatings may include chromium nitride, titanium-nitride, or other commercially available coatings such as ME92, Med Co 2000, or DLC. A suitable ferromagnetic substance is biocompatible, for example, a platinum-cobalt alloy may be used. Where the magnet material is biocompatible, the impeller need not be coated with a biocompatible material. In one embodiment, the impeller consists of a plurality of raised solid or hollow bodies having a combination of plane and curved side-wall surfaces, the bodies being spaced apart around the impeller periphery. The outer peripheral side wall of each of the bodies is convex in the radial direction with a radius of curvature that corresponds to the overall circular circumference of the impeller. The plane surfaces are flat, and two straight side walls are of unequal length. The side walls of unequal length extend inwardly from the convex peripheral side wall of the body to intersect at angle of approximately 90 degrees. The impeller bodies are similarly shaped. In each case their volume increases from the point of intersection of the two straight side walls to their convex peripheral side wall. The impeller is centrally open thereby defining an axial blood flow passage to the bottom wall of the pumping chamber. The intersecting side walls of the impeller bodies are rounded to minimize thrombosis and hemolysis. The impeller bodies are spaced apart by fluid flow paths therebetween that are defined by the sidewalls of the raised bodies. The impeller bodies may be magnetized to interact with magnetic forces imposed by the motor stators to permit the impeller to be rotated within the pumping chamber. The impeller is magnetically and hydrodynamically suspended from contact with the pump housing both radially and axially when the pump is operating. Hydrodynamic axial thrust forces acting in one direction are created during operation of the pump by at least one inclined or tapered surface area formed on an upper projection surface of at least one of the raised bodies adjacent to an internal surface of the upper pump casing. In some embodiments one of such bearing surfaces may be formed on each of the upper projection surfaces such that a plurality of such tapered surface areas may be utilized, as desired. Each such tapered surface area defines a hydrodynamic bearing surface. As the impeller rotates, blood engages the bearing surfaces at a relatively low pressure leading end of the bearing surface and is compressed against the internal surface of the upper pump casing by the inclined bearing surface which thereby creates a higher pressure exit or trailing end, causing an increase in fluid pressure acting axially on the impeller. Shrouds may be formed on the inner and outer sides of the tapered surface area to prevent fluid leakage. A pressure relief surface may be formed on the impeller downstream of and adjacent the exit end of each inclined bearing surface. The pressure relief surface is tapered to diverge from the inclined bearing surface thereby forming an area of lower fluid pressure to permit the blood to be directed into one of the several fluid flow paths between the raised bodies of the impeller. The bottom of the impeller is covered by a substantially flat, smooth disk parallel to the bottom wall of the pumping chamber. Each flow path between adjacent impeller bodies is substantially uniform in circumferential width. The longer side wall of one impeller body faces the shorter side wall of an adjacent impeller body across and defining a fluid flow path therebetween. The longer and shorter side walls define the sides of each of the fluid flow paths. In this embodiment, the longitudinal axis of each flow path defines an angle with the longitudinal axis of each of the flow paths adjacent to it on either side of approximately 90 degrees.

Alternatively, the impeller bodies may be formed as hollow titanium casings. Each such casing defines an interior cavity which may be fitted with a permanent magnet. Each inserted magnet is held within its associated cavity by a cap element or by a circular disk that covers the bottom of the impeller. In either case, the cap or disk is hermetically sealed to the casing, such as by laser welding. Solid walls between the hollow casings may contain a plurality of bores to modify the weight of the impeller and to provide consistent rotation. A passive magnetic bearing provides radial impeller support for rotation of the impeller around a center post within the housing without contact with the post during operation of the pump. In one embodiment, the magnetic bearing for the impeller is created by repulsive forces of magnetic vectors provided by corresponding permanent magnets. Magnetic vectors created by one or more such permanent magnets located within the impeller are adapted to repel magnetic vectors resulting from one or more permanent magnets located within the center post around which the impeller rotates without contact during pump operation. Such an arrangement provides radial stiffness for the rotating impeller and leaves an open space between the impeller and the center post which defines a portion of another of several fluid flow paths through the impeller.

In one embodiment, the axial alignment between the magnets within the impeller and the magnets within the center post is adjustable to provide repulsive magnetic preload forces acting on the impeller in an axial direction opposite to the axial forces imposed on the impeller as a result of hydrodynamic thrust. The magnetic preload enables the impeller to avoid contact between its bottom surface and an interior surface of the lower pump casing. This ensures yet another blood flow path around the impeller which enables fluid pressure within the pumping chamber to keep blood below the impeller in motion since blood is moved from beneath the impeller up through the annular space between the impeller and the center post around which it rotates. The magnetic preload may also be sufficient to restore the impeller to its original position should it undergo a significant shock event. Motor electromagnetic forces may also provide supplemental axial magnetic preload as well as supplemental radial impeller support. Magnetic preload enables the impeller to avoid contact between its bottom surfaces and the lower interior surface of the lower pump housing casing. During operation, the axial force produced by hydrodynamic thrust bearing surfaces on the upper projection surfaces of the impeller bodies moves the impeller away from the upper wall of the housing but permits a blood flow path between the lower projection surfaces of the impeller and the lower wall of the housing. Fluid pressure within the pumping chamber keeps blood in motion below the impeller. Blood may move from beneath the impeller up through the open center of the impeller as the impeller rotates.

In one embodiment, the motor stators are concentric with the impeller and have substantially the same diameter such that magnetic interaction between the motor stators and magnetic regions of the impeller assists in creating radial impeller stiffness. Axial preload on the impeller may also be provided by locating a motor stator on the upper pump housing casing in close proximity to the impeller. In a dual motor stator embodiment, axial preload on the impeller may be provided by locating the upper motor stator closer to the impeller than the lower motor stator. As a result of balanced forces acting in axially opposite directions on the impeller and the unique structure of the impeller, the impeller is effectively dynamically suspended between the upper and lower casings of the pump housing during operation of the pump. Blood is thereby forced to move about the impeller and through the pumping chamber without hemolysis or thrombosis. It will be understood that magnetic forces may be provided by permanent magnets, by electromagnetic circuits or by a combination of both such sources of magnetic forces. As a result of preload and hydrodynamic forces acting in axially opposite directions on the impeller and the unique structure of the impeller, the impeller is effectively dynamically suspended between the upper and lower casings of the pump housing during operation of the pump. Blood is thereby forced to move about the impeller and through the pumping chamber without hemolysis or thrombosis. It will be understood that magnetic forces may be provided by permanent magnets, by electromagnetic circuits, by magnetization processes or by a combination of such sources of a magnetic flux field.

The method of operation includes apical implantation of a short inflow cannula into the left ventricle of a heart, pressurizing the inflowing blood fluid within a pumping chamber by causing rotation therein of an impeller without mechanical contact with the impeller, positioning the rotating impeller to be suspended within the chamber so as to be completely submerged in the inflowing blood fluid, causing the inflowing blood fluid to traverse at least three flow paths within and around the impeller whereby pressure within the pumping chamber causes continuous flow of the blood from the inflow to an outflow from the pumping chamber, and directing the outflowing blood through a tube graft to the aorta.

BRIEF DESCRIPTION OF THE DRAWINGS

For a further understanding of the present invention, reference may be had to the accompanying drawings from which the nature and attendant advantages of the invention will be readily understood, and in which.

DETAILED DESCRIPTION OF THE INVENTION

Figure 1:
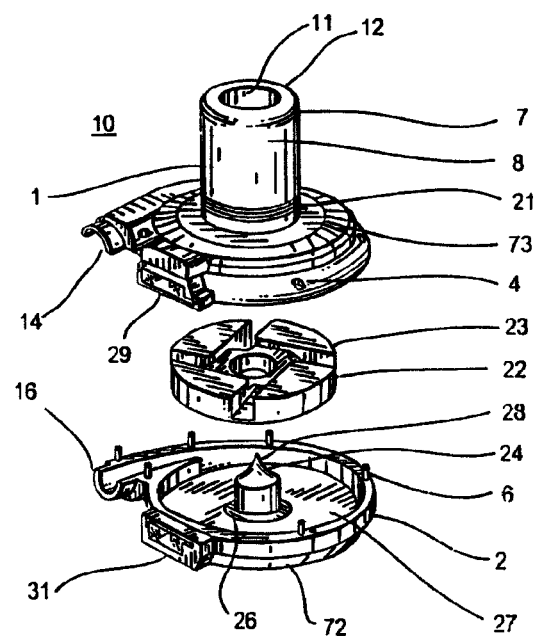
FIG. 1 is an exploded view of a rotary blood pump according to an embodiment of the present invention.

In describing the embodiments of the present invention illustrated in the drawings, specific terminology is employed for sake of clarity. However, the present disclosure is not intended to be limited to the specific terminology so selected, and it is to be understood that each specific element includes all technical equivalents which operate in a similar manner.

Figure 5:
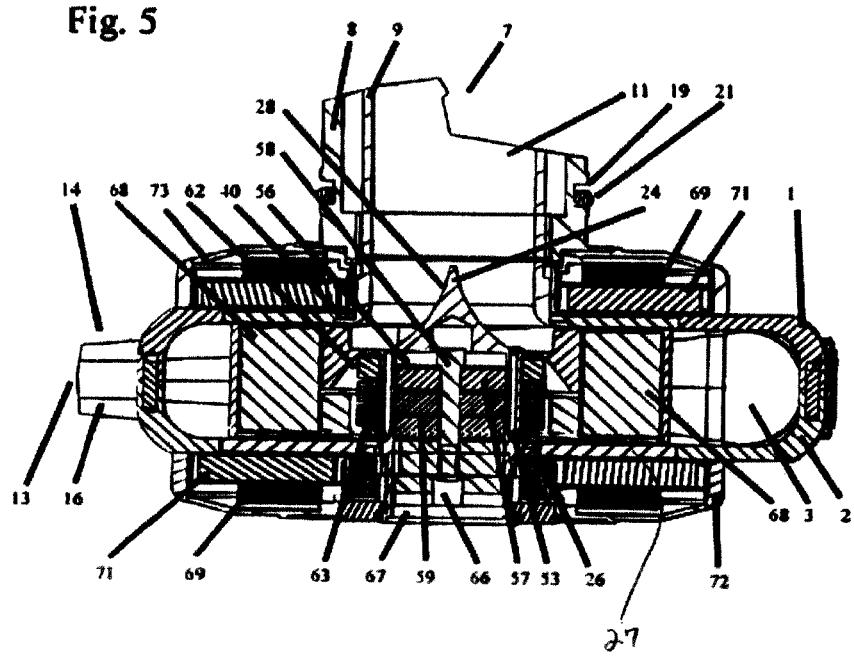
FIG. 5 is a cross-sectional view of an assembled rotary blood pump according to an embodiment of the present invention.

Referring now to FIG. 1 there is shown a rotary blood pump 10 having a pump housing that consists of a substantially circular front or upper pump casing 1 and a substantially circular rear or lower pump casing 2 of equal diameter that interlocks with the upper pump casing 1 to form a closed pumping chamber between them. The configuration of the upper and lower pump casings is such that the assembled pump housing defines a substantially cylindrical pumping chamber 3 therein (FIG. 5). In one embodiment the pumping chamber has a displaced volume of 45 cc. The upper pump casing 1 may have a plurality of peripheral positioning holes 4 for receiving a corresponding plurality of positioning pins 6 projecting from the periphery of the lower pump casing 2. The configuration of positioning holes 4 and positioning pins 6 ensures that the upper pump casing 1 and the lower pump casing 2 interlock in the correct position when the rotary blood pump 10 is assembled. The contact area between the upper pump casing 1 and the lower pump casing 2 may be sealed, for example using screws or a chemical sealant.

In the embodiment shown in FIG. 1 blood is supplied to the pump through an axial inlet cannula 7 adapted for apical insertion into a heart ventricle. The cannula 7 is affixed to or may be integral with the upper pump casing and is in fluid flow communication with the pumping chamber 3 of the pump 10. As shown in the cross sectional view of FIG. 5, an embodiment of the inflow cannula 7 is of two-piece design, consisting of an outer cylindrical section 8 and a coaxial inner cylindrical section 9. The outer cylindrical section 8 of the inflow cannula 7 maybe welded in an appropriate sealable manner to the outer surface of the upper pump casing 1. The inner cylindrical section 9 defines an inlet channel 11 for the blood when the pump is installed and in operation. The sections 8 and 9 may be laser welded together at the outer end 12 of the cannula, shown in FIG. 1. In one embodiment, the outside diameter of the outer section 8 is about 0.81 inches while the inside diameter of the inner section 9 is about 0.50 inches.

In one embodiment, the pumping chamber is in fluid-flow communication with a volute or diffuser section to avoid alteration of the position of the impeller in a radial direction as blood pressure increases during operation of the pump. The upper pump casing 1 and lower pump casing 2 together define the diffuser by a pair of complementary upper and lower half-round sections 14 and 16 formed as part of the upper and lower housing casings, respectively. The sections 14 and 16 together define a short open-ended cylindrical diffuser tube. The diffuser extends completely around the circumference of the pump terminating at a tangential outlet port 13 (FIG. 5). In one embodiment, the cross section of the diffuser section enlarges from an inlet end along its length to a maximum at the outlet 13. Blood exits the pumping chamber 3 through the outlet 13 in a direction substantially perpendicular to the longitudinal axis of the inlet cannula 7, an arrangement that has been found to be anatomically advantageous for locating the pump in the pericardial space. When the pump is installed and in operation, the outlet 13 is adapted to be joined to an outflow graft 17, shown in FIG. 9, which in turn is suitably connected to the aorta 18. In one embodiment, the pump housings or casings and the cannula may be made of titanium, a biocompatible titanium alloy, or a biocompatible ceramic material. The pump structure may be machined from titanium or an alloy thereof. Alternatively, the pump structure, including the cannula, may be formed entirely from ceramic material.

Sealing of the cannula 7 to the heart ventricle may be accomplished with the assistance of a peripheral ring groove (FIG. 5) formed in the outer cylindrical surface of the cannula near the upper pump casing 1. The ring groove is fitted with an annular O-ring to provide a leak proof seal to a sewing ring of a ventricular connector [not shown] of the type described, by way of example, in commonly owned U.S. Pat. No. 6,732,501. According to another embodiment, a peripheral ring groove is unnecessary and an O-ring surrounding the cannula may be incorporated into the sewing ring to ensure a leak proof seal.

With reference to FIG. 1, a motor rotor or pump impeller 22 is located within the pumping chamber 3 between the upper pump casing 1 and the lower pump casing 2. The impeller 22 is circular in cross section and may have a diameter of an inch or an inch and a quarter. The impeller is provided with a central hole 23. A center post or spindle 24 is attached to the lower pump casing 2 and protrudes from the axial center thereof through the impeller hole 23 when the pump is assembled to support rotation of the impeller in the manner described in detail below. The center post 24 is provided with a peripheral lower flange 26 by which a lower annular ceramic disc 27 is retained to an interior surface of the lower pump casing 2. In one embodiment, the gap between the outer diameter of the center post 24 and the diameter of the impeller hole 23 is in the range of from 0.019 inches to 0.029 inches. The top portion of the center post 24 is formed as a conical surface 28. A substantial portion of the conical surface 28 of the center post protrudes above the impeller hole 23 during operation of the pump. In one embodiment, the radius of curvature of the cone shape is a relatively constant 0.389 inches. The tip of the cone is not necessarily a sharp point having, in one embodiment, a blending radius of 0.010 inches.

In operation, blood entering the cannula 7 from a heart ventricle passes axially over the conical surface of the center post 24 into the pumping chamber 3 where it is engaged by the rotating impeller. Blood entering the pumping chamber from the cannula 7 is redirected from axial flow exiting the cannula to a radial flow within which the impeller 22 is submerged. The rotating impeller presses the blood radially into a whirling motion as a result of the configuration of the spinning impeller, described in detail below, and moves within the diffuser at the perimeter of the pumping chamber to the outlet 13.

Figure 10:
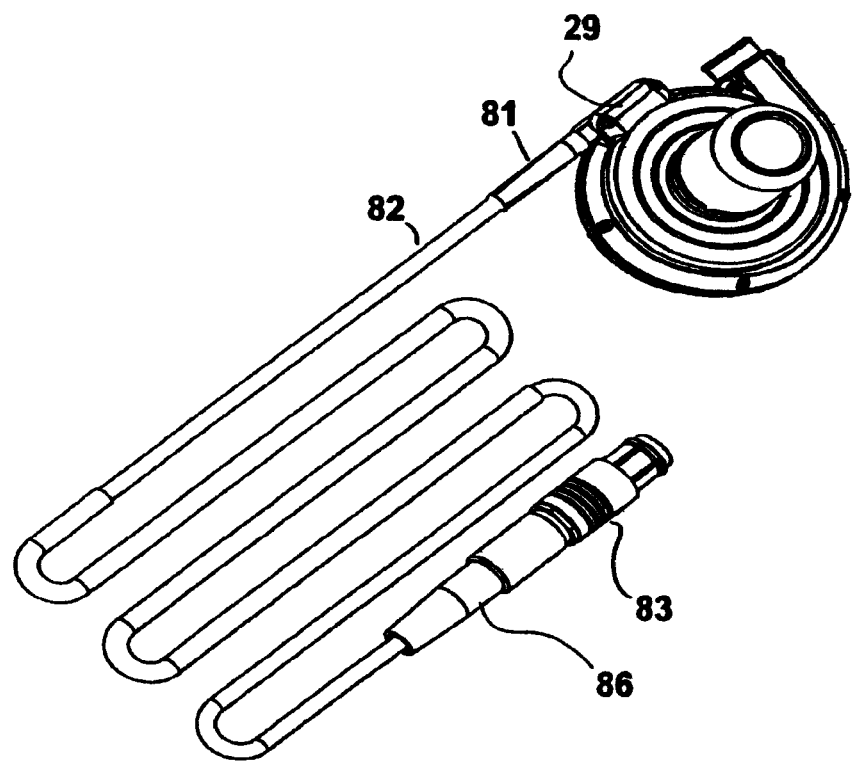
FIG. 10 is a top plan view of a rotary blood pump according to an embodiment of the present invention to which a pliable cylinder carrying power cables is attached.
Figure 11:
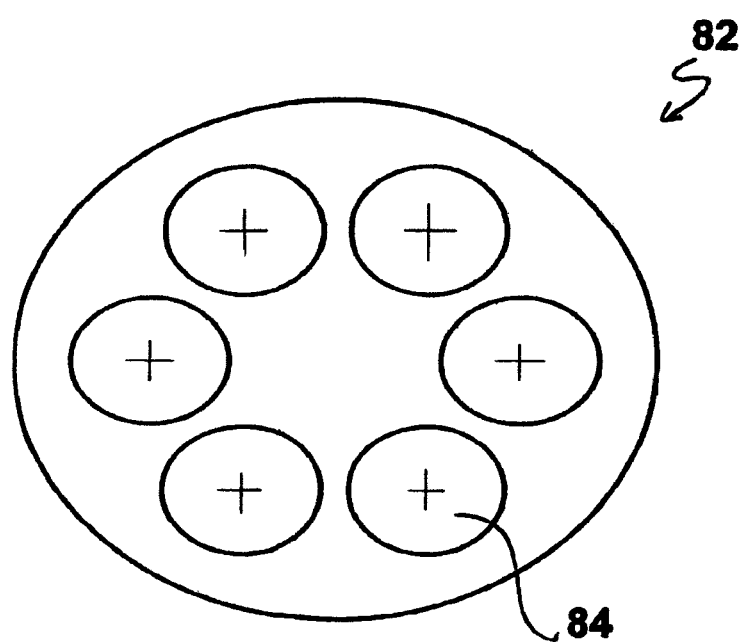
FIG. 11 is a cross section of the pliable cylinder of the present invention illustrating a plurality of lumen therein for carrying power cables.

The upper pump casing 1 may contain the upper half 29 of an electrical feed through connector and header for a power and control cable to supply power to the electrical motor of the pump. The lower pump casing 2 may contain a corresponding lower half 31 of the electrical header. When the pump is assembled, the upper and lower halves 29 and 31 interlock to form the header through which feed-through power wires are connected to the electromagnetic motor stators. In one embodiment, the feed-through wires are platinum. A PEEK header may be used to connect the feed through wires to the external drive cables. The header may be made of a material such as PEEK or a suitable plastic such as Tecothan or polysulfone. The header may also be made of a medical grade epoxy. With reference to FIG. 10, the upper half 29 of a PEEK front pump header is shown connected to the power line cable through a strain relief section 81. The strain relief section is, in turn, connected to a pliable elongated cylinder 82 which may be as long as desired to reach a suitable external power source, which may be the output of a controller (not shown). A connector and locking plug device for connection to the power source is affixed to the tubing 82 at its distal end. The pliable cylinder is adapted to carry a plurality of power cables to carry electrical power to the pump. In one embodiment the pliable cylinder is made of silicone. The pliable cylinder may be covered by a thin urethane sheath (not shown) for extra abrasion resistance. It will be understood by those skilled in the art that other bio-compatible materials such as urethane may be used for the pliable cylinder without departing from the scope of the present invention. Referring to FIG. 11, the pliable cylinder 82 contains a plurality of lumens 84 having circular cross sections, through each of which individual power cables are threaded. In one embodiment there are six such lumens spaced around the center of the cylinder adjacent its periphery in a generally circular configuration. The centers of each lumen are approximately 60° apart. In one embodiment, the diameter of the pliable cylinder is about 0.138 inches and the diameter of each lumen is approximately about 0.034 inches. Such lumens can be used to hold power cables having a diameter of about 0.029 inches. The use of individual lumens within the cable tubing 82 has the benefit of extra fatigue resistance because the individual power cables cannot rub together. In addition, when replacement is necessary replacement in situ is enabled since one power cable at a time may be replaced in order to minimize any stop time of the pump. A strain relief mechanism 86 may be used adjacent the distal connector and locking plug device.

Figure 2:
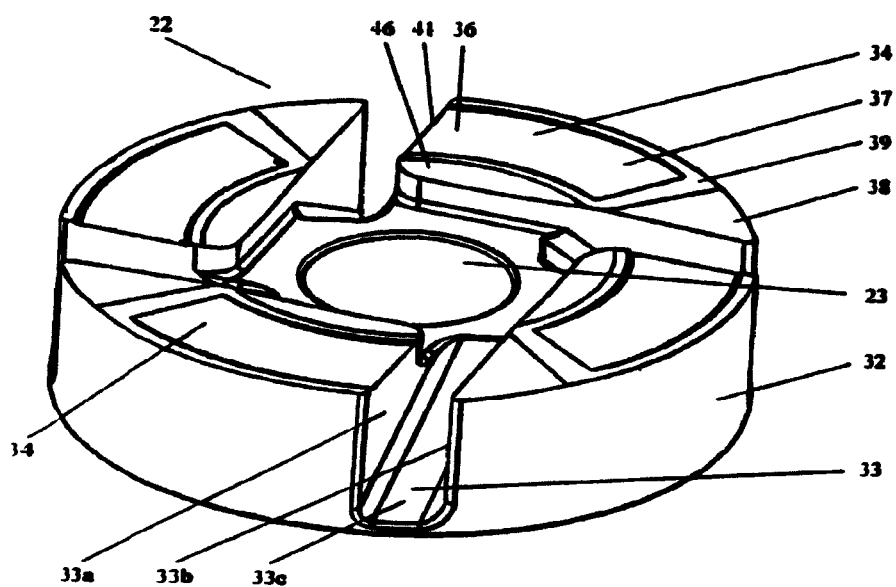
FIG. 2 is a perspective view of the outer surface areas of an impeller according to an embodiment of the present invention.

Referring now to FIG. 2 the impeller 22 is shown in greater detail. In this embodiment, the impeller is substantially circular in cross section and has a plurality of identical substantially hollow raised bodies 32 circumferentially arranged thereon. Each of the raised impeller bodies 32 has a generally right triangular cross section in a horizontal plane, with a curved hypotenuse defining a portion of the circumference of the impeller. In one embodiment there are four such raised impeller bodies, the mid points of which are approximately 90 degrees apart.

The raised impeller bodies 32 are separated by flow slots or channels 33 adapted to permit the flow of blood from the central portion of the impeller to the surrounding pumping chamber. In one embodiment, the width of each of the slots 33 is about 0.150 inches. The flow slots 33 are defined by vertical planar sidewalls 33a and 33b of unequal length extending parallel to but offset from a diameter of the impeller. In one embodiment, the sidewall closest to the diameter of the impeller, for example the sidewall 33a of FIG. 2, is offset from the diameter by about 0.164 inches. Each of the slots 33 has a downward-sloping bottom surface 33c, which constitutes an inclined ramp forming an angle of about 32 degrees with the horizontal. The exit points of the flow slots 33 at the circumference of the impeller are approximately 90 degrees apart. Each ramp surface 33c is longitudinally at right angles with the corresponding longitudinal axis of the flow slots on either side.

The primary flow path for blood entering the inflow cannula 7 is to strike the conical surface 28 of the center post 24 and pass through the flow slots or channels 33 to fill the pumping chamber. As indicated, the rotating impeller causes the fluid pressure in the pumping chamber to increase resulting in continuous movement of the blood from the inflow 11 to the outflow port 13.

The upper surface of each impeller body 32 is provided with a curved and tapered or inclined ramp 34 defining an axial hydrodynamic bearing surface. In one embodiment, each ramp surface 34 spirals upward in a clockwise direction from a relatively lower fluid pressure entrance region 36 to a relatively higher fluid pressure exit region 37. The angle of inclination of the bearing surface 34 is less than one degree relative to the horizontal. When the impeller 22 is rotating, the sidewalls 33a define leading edges so that blood passing over the hydrodynamic bearing surfaces is compressed with increasing force against the adjacent interior surface of the upper pump casing 1 with result that a net axially downward pressure is exerted on the upper projection surface of each raised impeller body. In operation, the thickness of the blood layer between the bearing surfaces 34 and the adjacent housing surface is a function of the fluid viscosity, the impeller rotational speed and the geometry of the impeller bearing. As the fluid viscosity increases the fluid layer thickness increases. As the rotational speed increases the fluid layer thickness increases and, because of the net axial hydrodynamic pressure on the impeller and the fact that the impeller is suspended within the pumping chamber in part by a magnetic preload described below, the distance from each bearing surface 34 to the adjacent upper casing face can change with rotational speed and fluid viscosity. However, in one embodiment that distance will be within the range of from 0.003 inches to 0.020 inches.

Each raised impeller body 32 may also have wedge-shaped region forming a pressure relief surface 38 downstream of the bearing surface 34. The pressure relief surface 38 ensures a controlled and predictable lowering of the hydrodynamic pressure to minimize the blood shear stress and hemolysis. In addition, each pressure relief surface assists in defining a secondary flow path for blood within the pumping chamber whereby blood exiting a bearing surface 34 is re-entrained across the adjacent pressure relief surface into the next downstream impeller flow slot or channel 33, and from there into a lateral annular space defining the diffuser portion of the pumping chamber.

A relatively flat surface area on the upper surface of each impeller body defines a substantially planar bridging surface 39 between each exit end 37 of a bearing surface 34 and the associated pressure relief surface 38. In one embodiment, the width of each of the bridging surfaces 39 at its narrowest point is about 0.050 with a reasonable tolerance of ±0.028 inches. In such an embodiment, the pressure relief surface 38 may be inclined relative to the horizontal at an angle of from 2 to 4 degrees.

Figure 3:
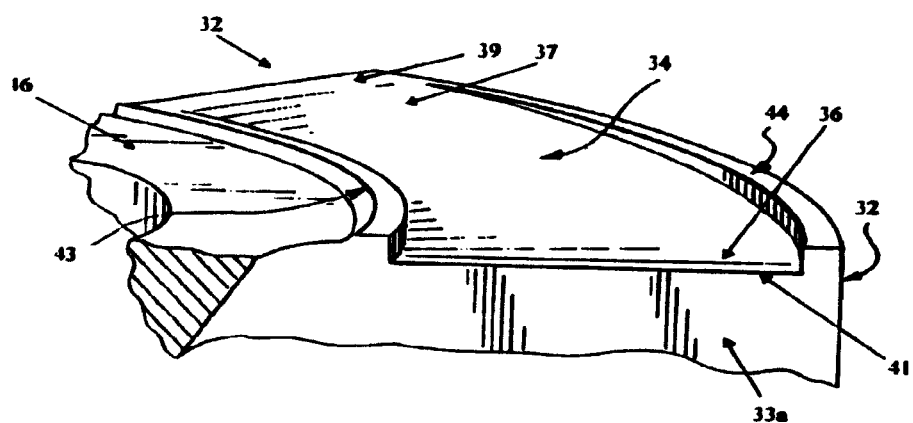
FIG. 3 is a perspective view of a section of the outer surface area of the impeller of FIG. 2 which contains a hydrodynamic bearing surface.

Referring now to FIG. 3 there is shown in perspective one of the hydrodynamic bearing surfaces 34. Each bearing surface is of approximately uniform width from the entrance region 36, which defines a junction edge 41 with the leading substantially vertical sidewall, for example sidewall 33a of the slot 33 (FIG. 2), to the exit region 37. In one embodiment, the junction edge 41 is relatively sharp, having a maximum radius of curvature of less than 0.010 inches, and may be as small as 0.005 inches or smaller. As indicated, each bearing surface 34 is inclined upwardly from the entrance end 36 at an angle of less than 1 degree relative to the horizontal and terminates at approximately the flat bridging surface 39.

In one embodiment, each bearing surface 34 is bounded along its length on opposite sides by inner and outer shrouds 43 and 44, respectively. The outside surface of the outer shroud defines a portion of the peripheral surface of the impeller. In operation, the inner shroud 43 and the outer shroud 44 effectively minimize the fluid leaking out of the sides of the bearing surfaces thereby assisting the retention of blood engaging the bearing surface to maximize the fluid layer thickness and minimize the fluid shear stress. The shrouds also serve to guide the blood toward the exit end 37 of the bearing surface from which it flows over the pressure relief surface 38 and into the next downstream flow slot 33. The top surface of each of the shrouds 43 and 44 is relatively planar or flat and, in one embodiment, each has a width of not less than 0.020 inches. The top surface of each of the shrouds 43 and 44 may be higher than the entrance end 36 of the bearing surface 34 by about 0.230 inches. At the exit end 37 of the bearing surface, the top surface of the shrouds 43 and 44 and the bearing surface may merge into the planar bridging surface 39.

In one embodiment, there is formed on each of the raised impeller bodies 32 an inwardly facing and downwardly tapered curved section 46 inside of the inner shroud 43. The axial drop distance for each section 46 is about 0.012 inches and the angle of taper is about 8°. The section 46 assists in directing blood deflected from the conical surface 28 of the central post 24 to the central portion of the impeller, which then flows from there into the slots 33 formed between the impeller bodies 32.

The inner surface of the upper pump casing 1 is provided with an upper annular ceramic disk (not shown) similar to the lower ceramic disc 27 on the inner surface of the lower pump casing 2. The upper ceramic disk serves to minimize friction on start-up of the pump. An annular flange 40 formed at the inner end of the inner cylindrical section 9 of the cannula 7 (FIG. 5) serves to retain the upper ceramic disc in place. The ceramic disks reduce electrical losses between the motor stators (described below) and the rotor magnets within the impeller, as well as provide very flat surfaces for the hydrodynamic thrust bearings on the impeller top surface. When the impeller is at rest it sits against the surface of the upper ceramic disc. When rotational speed is imparted to the impeller during startup, the impeller lifts off of the upper ceramic disc and becomes fully suspended as described below. The impeller may be coated with titanium nitride to minimize wear during the starting and stopping process of the pump.

The impeller may be a single integral structure made of a magnetically isotropic alloy. The material of a one-piece impeller of the type described above may be biocompatible to avoid having to coat the impeller or sub-assemblies. An example of a suitable magnetically isotropic biocompatible material is an alloy of approximately 77.6% platinum (by weight) and 22.4% (by weight) cobalt. Such a one-piece impeller may be easier and less expensive to manufacture than impellers formed from multiple parts. Each raised impeller body 32 may have a magnetized portion. Magnetization of such an impeller may be performed by techniques known in the art, such as the exposure to a relatively strong magnetic field. In one embodiment, the raised projection surfaces of each of the impeller bodies may be magnetized to provide magnetic poles. The magnetic poles of the impeller couple magnetically with magnetic poles provided by motor stators 69 (FIG. 5) thereby enabling one or both of the stators to provide both a magnetic drive force to cause the impeller to rotate within the pumping chamber and magnetic axial and radial support. In one embodiment, every other upper projection surface is magnetized to the same magnetic pole while the projection surfaces therebetween are magnetized to have the opposite magnetic pole. For example, where an upper projection surface has a North magnetic pole each projection surface on either side has a South magnetic pole. The particular arrangement of magnetic poles may be determined as desired without departing from the scope of the present invention. It will be understood that the motor stator coils that drive the impeller provide magnetic poles in a pattern complementary to those employed on the impeller.

Figure 4:
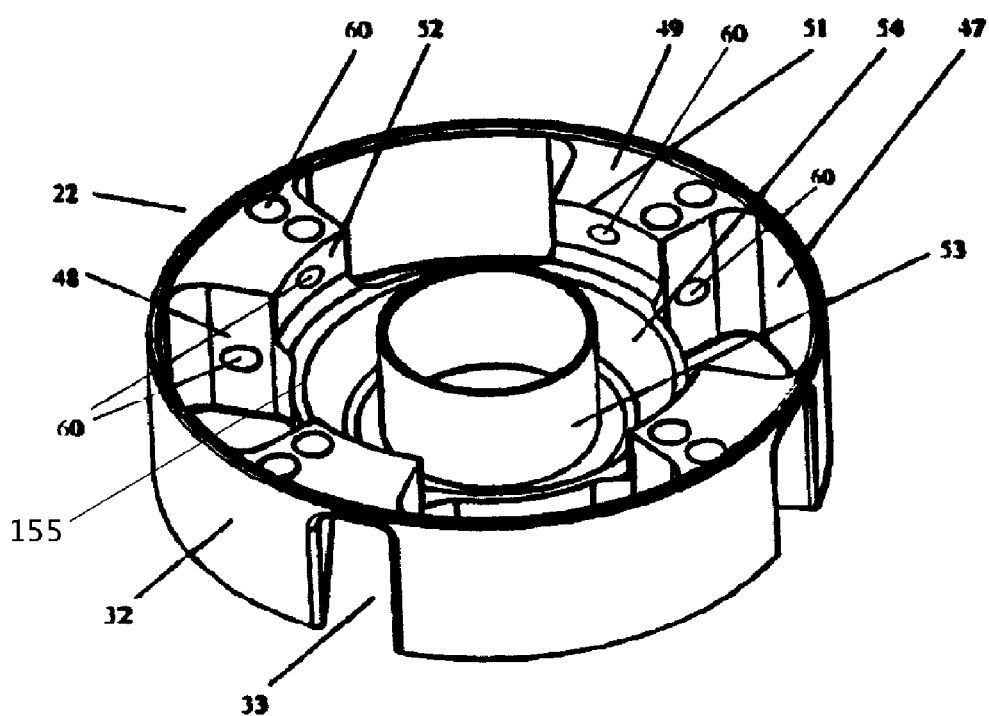
FIG. 4 is a perspective view of the underside of the impeller of FIG. 2.

Referring now to FIG. 4, there is shown in perspective the underside of the impeller 22 in which each raised impeller body 32 is hollowed out to define a plurality of interior cavities or pockets 47. In cross section, each pocket 47 substantially corresponds in size and shape to the raised impeller body which defines its boundaries. The upper projection surface of each such raised impeller body contains a hydrodynamic bearing surface which defines the top of the interior cavity therebeneath. In one embodiment, the outer curved boundary of each of the pockets is concentric with the impeller and subtends an angle relative to the center of the impeller of about 56.5 degrees. The inner radius of each such pocket relative to the center of the impeller is about 0.4 inches and the outer radius is about 0.665 inches. The pockets are located about 90 degrees apart around the periphery of the impeller.

As described in detail below, the pockets 47 are adapted to receive rotor magnets forming part of the motor drive system for the impeller. The pockets 47 are separated by a plurality of substantially equally sized inwardly projecting wall members 48 integrally formed with the impeller and defining substantially horizontal flat lower surfaces or shelves 49 terminating radially inwardly at curved edge portions 51. In one embodiment, there are four such wall members, each of which is situated between two pockets. Each wall member and pocket is situated diametrically opposite a corresponding wall member or pocket. The edge portions 51 define a boundary of a substantially vertical inwardly facing curved surface 52, substantially concentric with the circumference of the impeller.

A hollow cylinder 53 projects axially inwardly and defines the central hole 23 of the impeller. In one embodiment, the central hole has a diameter of about 0.437 inches. When the pump is assembled, the center post 24 extends through the cylinder 53 into the pumping chamber. In one embodiment, the radial gap between in the inner diameter of the cylinder 53 and the outer diameter of the center post 24 is about 0.022 inches.

An annular cavity or space 54 is formed between the hollow cylinder 53, the curve surfaces 52 and a radially outermost open-ended cylinder 155 that is concentric with cylinder 53. A space between the cylinder 53 and an inner surface area of the outermost open-ended cylinder 155 defines an annular groove portion of the annular space 54. In this embodiment, the annular cavity 54 has an inside diameter of about 0.437 inches, an outside diameter of about 0.575 inches, and is adapted to receive passive magnetic bearing components, as described in detail below.

At least one of the wall members 48, 49 or 52 may be provided with one or more balancing holes or bores 60 which are formed to ensure a balanced and even rotation of the impeller during operation of the pump. In one embodiment a wall member is provided with a set of two balancing holes of unequal depth and approximately equal diameters situated side-by-side along a radius of the impeller. In this embodiment, the depth of the balancing hole closest to the center of the impeller is about 0.10 inches, while the depth of the outermost balancing hole is about 0.25 inches. Each set of holes is situated diametrically opposite another set, whereby the diametric distance between the outermost holes of two opposite sets of holes is about 1.22 inches and the diametric distance between the inner most holes of the sets is about 1.02 inches.

With reference to FIG. 5, there is shown a cross-sectional view of an assembled rotary blood pump according to an embodiment of the present invention. The upper casing 1 has affixed thereto the inflow cannula 7 with its inlet channel 11. The outflow port 13 is formed by joinder of the half-round tubular extensions 14 and 16. The center post 24 extends upwardly into the pumping chamber through the bottom of the lower casing 2.

Figure 6:
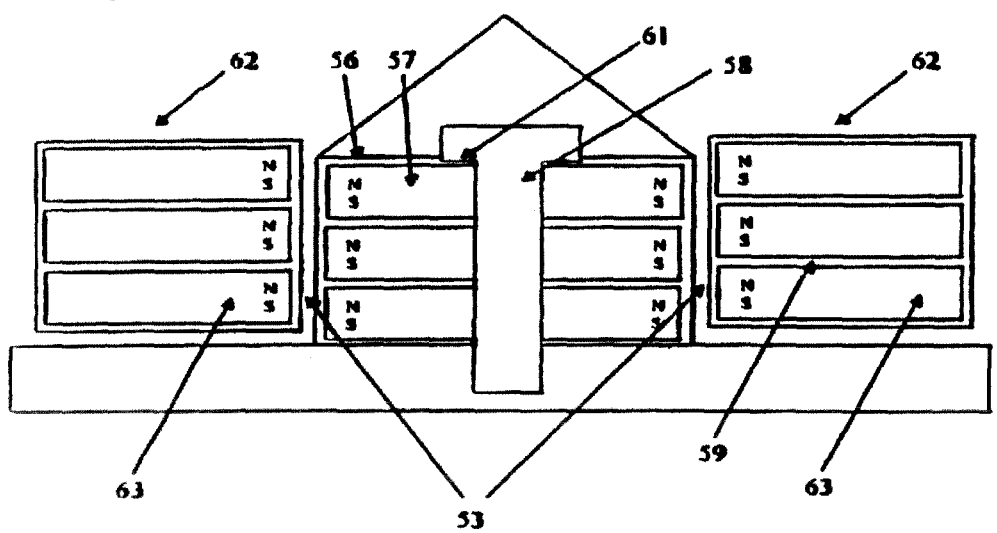
FIG. 6 is a sectional view of a portion of a passive magnetic bearing structure for an impeller according to an embodiment of the present invention.

With reference to FIGS. 5 and 6, in one embodiment an impeller suspension system utilizes a passive magnetic bearing to provide radial impeller support with respect to the center post 24. The passive magnetic bearing is adjustable to provide an axially directed magnetic preload adapted to be resisted by the forces generated by the hydrodynamic thrust bearings described above in connection with each of the impeller blades 32. In one embodiment, one portion of the passive magnetic bearing is formed by a stack 56 of permanent bearing magnets 57 enclosed within the center post 24. The stack 56 may consist of three ring-shaped permanent magnets 57 placed one on top of the other and coaxially aligned along the axis of rotation of the pump impeller 22. Each of the ring magnets 57 has an axial height of less than 0.10 inches, and an outer diameter of about 0.34 inches.

In one embodiment, and as seen best in FIG. 6, each of the three center post bearing magnets 57 may provide a magnetic vector oriented in the axial direction, for example either north-on-top, south-on-bottom (N-S) or south-on-top, north-on-bottom (S-N). Thus, the stack of center post bearing magnets 57 may have alternating magnetization such that the polarizations of the magnets within the stack may be N-S, S-N, N-S or S-N, N-S, S-N, as desired, whereby the magnetic forces established by each ring shaped magnet 57 of the stack 56 act to repulse its adjacent magnet in the axial direction.

As there are repulsive forces between each magnet, the magnets may be fixed to or otherwise mechanically held in their coaxial relationship by suitable engagement with an axially positioned center post rod 58. To ensure that the ring magnets are held in place, each magnet may be provided with a thin ring-shaped spacer or washer 59 on the top and the bottom of the magnet, the upper most spacer being engaged beneath a protruding circular flange 61 formed near the top of the center post rod 58 to assist in holding the magnets in their coaxial arrangement. The spacers 59 may also function to minimize demagnetization caused by the proximity of the stacked magnets. In one embodiment each such spacer would have a thickness of less than 0.015 inches. Alternatively, where desired, the spacers may be adapted to act as flux concentrators for re-directing and concentrating in the radial direction the magnetic flux produced by the magnets 57. Alternative embodiments for the magnetic vectors of the permanent magnets forming the stack 56 within the central post 24 may be employed without departing from the scope of the present invention. For example, the N-S orientations may be radial, with North on the left and South on the right.

The other portion of the passive magnet bearing for the impeller is formed by another stack 62 of ring-shaped permanent magnets 63 placed within the impeller and surrounding the cylinder 53. The stack 62 may consist of three ring-shaped permanent magnets 63. As shown in FIG. 6, each impeller bearing magnet 63 has a magnetic vector oriented in the axial direction with, for example, either north-on-top, south-on-bottom (N-S) or south-on-top, north-on-bottom (S-N). In one embodiment, the magnet pole arrangement of the stack of impeller magnets 63 corresponds to the magnetic pole arrangement of the stack of center post bearing magnets 57. Thus if the stack of center post bearing magnets 57 has its magnetic vectors oriented N-S, S-N, N-S then the magnetic vectors of the adjacent stack 62 of impeller magnets 63 may also be N-S, S-N, N-S. Provided there is a sufficient radially oriented magnetic flux concentration, such an arrangement of magnetic vectors, and others, would effect repulsive forces between the corresponding stacks 56 and 62, thereby establishing, in operation, a radially acting magnetic bearing between the rotating impeller and its fixed center post. In one embodiment, the inner and outer diameters of the ring-shaped magnets 63 within the impeller are about 0.44 inches and 0.52 inches, respectively, while the radial distance between the ring-shaped magnets 63 within the impeller and the ring-shaped magnets 57 within the center post 24 is about 0.050 inches.

With reference to FIG. 5, in one embodiment, the axial alignment of the center post magnet stack 56 with respect to the impeller magnet stack 62 may be adjustable so as to provide a selected axial preload force that biases the impeller toward the upper casing 1. In one embodiment, the flange 26 on the center post 24 holds the center post in position relative to the lower pump casing 2. The center post rod 58 extends upwardly through the center post and is axially movable within the center post by an appropriate adjustment screw 66 which threadably engages the lower end of the rod 58. Appropriate thread density could be on the order of 64 threads per inch.

The adjustment screw has a cap 67 engageable from beneath the impeller to adjust the axial position of the center post rod 58 and thereby the alignment of the impeller and center post bearing magnets. Thus, the center post rod 58 may be moved downwardly, for example, thereby moving the center post magnet stack 56 downwardly relative to the impeller magnet stack 62, as shown in FIGS. 5 and 6. When the misalignment between the corresponding magnet stacks 56 and 62 reaches approximately that shown in FIGS. 5 and 6, it will be apparent that repulsive forces between the N-S, S-N, N-S magnetic vectors of the impeller stack and the N-S, S-N, N-S magnetic vectors of the center post stack will provide a preload axial force that biases the impeller toward the upper pump casing 1 and assists in keeping the impeller running near the inner surface of the upper casing. When the desired magnet alignment is established, the cap 67 may be welded to the center post to establish a hermetic seal and to prevent inadvertent movement of the adjustment screw. The adjustment screw is thereby sealed at the outside surface of the lower pump casing 2. Other mechanical arrangements suitable for adjusting the axial position of the stack 56 may be adopted without departing from the scope of the invention.

When the pump is activated, the axial upwardly directed magnetic preload force caused by the offset between corresponding stacks of bearing magnets is balanced against the downward force in the axial direction created by the hydrodynamic thrust bearings on the impeller upper surface. Therefore, the impeller may be suspended in both the axial and radial directions and is submerged within the blood filling the pumping chamber. The inner and outer magnet bearing assemblies 56 and 62 thus work together to provide primary radial and axial stiffness to avoid wear and to ensure the presence of yet another open flow path for the blood being moved through the pump. This flow path is from the housing where the fluid collects after exiting the impeller flow slots 33, underneath the impeller and up through the annular gap between the center post and the impeller that is maintained by the passive magnetic bearing described above, from where the blood is re-entrained through the impeller flow slots 33 into the primary flow path described above. The impeller hydrodynamic thrust bearings described above provide axial stiffness only when the impeller is running near the inner surface of the upper casing 1.

Figure 7:
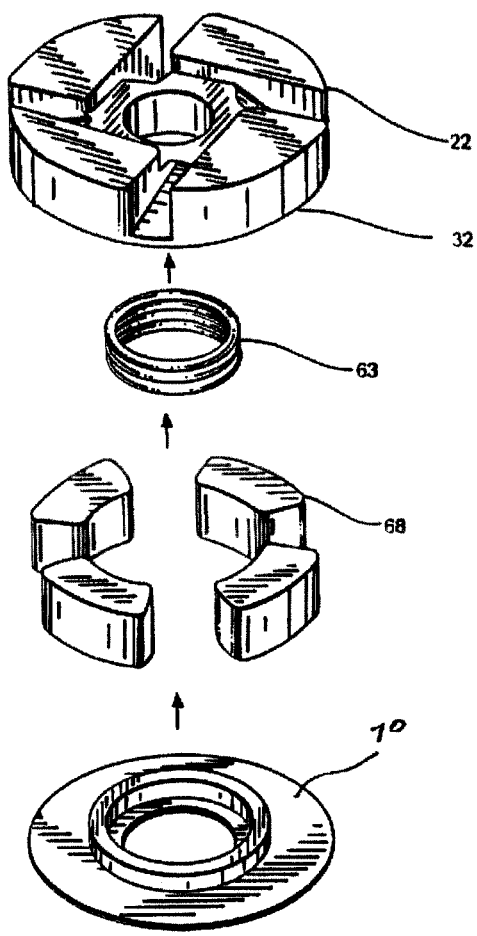
FIG. 7 is an exploded view of a magnetic assembly for supporting and driving an impeller according to an embodiment of the present invention.

As indicated above, the pump of the present invention may include a three-phase dual stator axial flux gap motor for driving the impeller. An advantage of a dual stator motor is that one of the stators may be used to cause the impeller to rotate should the other stator fail to function. In one embodiment, the lower stator is spaced farther from the impeller 22 than the upper stator so as not to degrade a net axial preloading of the impeller resulting from its magnetic interaction with the upper stator. With reference to FIGS. 5 and 7, the impeller is provided with a set of four drive magnets 68. Each drive magnet 68 is contained within one of the pockets or cavities 47 (FIG. 4) formed within the raised portions 32 of the impeller at the underside of the impeller. The drive magnets 68 are enclosed within the impeller by a suitable annular base plate 70.

Figure 8:
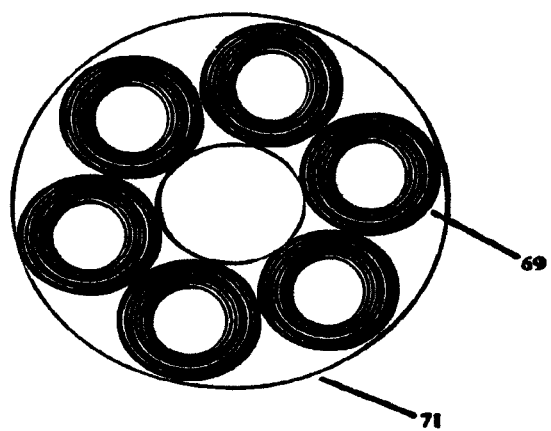
FIG. 8 is a top plan view of a motor stator according to an embodiment of the present invention.

As shown in FIG. 5, one stator is located above the impeller on the upper pump casing 1 while the other stator is positioned below the impeller on the lower pump casing 2. Each stator contains a plurality of the motor drive windings and a back iron ring 71. The motor drive windings 69 consist of coils of electrically conductive wire and may be circular in cross section or have other appropriate cross-sectional configurations, as desired. In one embodiment shown in FIG. 8, the coils are circular in cross section and each stator consists of six such coils placed on the outside of the respective back ring. The coils are placed on the back ring such that the coil axis is perpendicular to the surface of the ring. As will be understood by those skilled in the art, the motor drive coils 69 generate electromagnetic fields that interact with the magnetic fields of the impeller drive magnets 68 to cause the impeller to rotate. The back iron ring 71 serves to enhance the magnetic flux produced by the drive magnets. The magnetic forces produced by the motor stator coils also provide secondary radial impeller and axial magnetic preloading support to the impeller. The result is that the impeller is dynamically balanced in both the radial and axial directions during normal operation. It will be understood that only a single stator is needed to operate the pump motor of the present invention. Two stator assemblies are desirable because if one stator assembly should fail, the other will operate the motor, although operating power consumption will be increased.

Each stator is contained within a stator can 72, 73. Each stator can is hermetically sealed to its respective pump casing and, in one embodiment, has a thin wall less than 0.007 inches thick closest to the motor drive magnets 68. The thin wall allows the use of the ceramic discs between the impeller and the stators. Each stator can has a hermetic feed-through arrangement for the electrical connections to the conjoined external headers or connectors 29 and 31.

Figure 9:
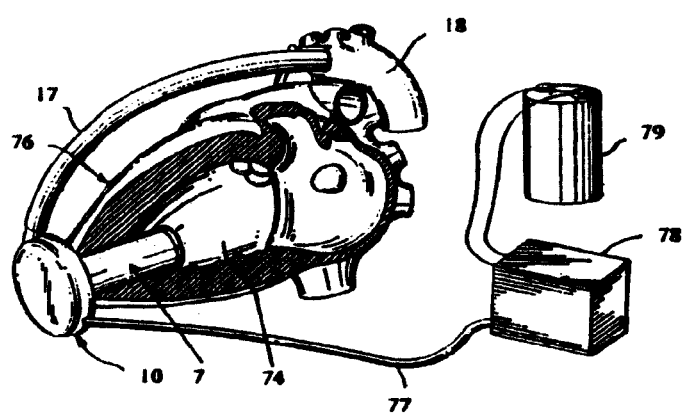
FIG. 9 is a system view of an implanted rotary blood pump according to an embodiment of the present invention.

FIG. 9 illustrates an implanted rotary blood pump according to an embodiment of the present disclosure. The inflow cannula 7 is inserted apically into the left ventricle 74 of the patient's heart 76. A blood transport graft or tube 17 connects the blood outlet of the rotary blood pump to the patient's aorta 18. The power and control cable 77 may be connected to a controller 78 having a power source 79. The controller 78 and the power source 79 may be implanted within the patient's body or worn by the patient. The controller is used to provide clinicians information on how the device is performing, to provide run status and alarm conditions and controls the rotational speed of the impeller, as may be desired. For example, impeller rotational speed may be controlled by using a pulsed drive waveform and measuring the back emf of the rotor when the drive pulse is at zero. Such a technique is set forth in commonly owned International Application No. PCT/US00/40325 having an International Publication Number WO 01/05023 A1, incorporated herein by reference.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. A rotary blood pump comprising:
   a housing defining a pump chamber; and
   an impeller rotatable on a rotation axis within said pump chamber, said impeller having a hollow interior cavity defined by a cylindrical perimeter wall surface, and a plurality of spaced apart polyhedron bodies within said interior cavity each extending radially inwardly from said perimeter wall surface and having a surface area facing the rotation axis of said impeller, said polyhedron bodies being positioned to enable balanced rotation of said impeller, selected polyhedron bodies comprising one or more openings formed in predetermined surface areas thereof and configured substantially to equalize the weight thereof, the impeller further including a base covering the interior cavity such that the polyhedron bodies and the openings therein are enclosed within the interior cavity covered by the base.

2. The rotary blood pump of claim 1 comprising at least two of said polyhedron bodies spaced approximately 180 degrees apart about the rotation axis of said impeller.

3. The rotary blood pump of claim 1 comprising four of said polyhedron bodies spaced approximately 90 degrees apart about the rotation axis of said impeller.

4. The rotary blood pump of claim 1 in which each polyhedron surface area facing the rotation axis of the impeller is curved, said curved surfaces areas having equal radii of curvature such that collectively said curved surface areas define a common circular arc the center of which is the rotation axis of the impeller.

5. The rotary blood pump of claim 4 comprising a plurality of open-ended cylinders of unequal diameters extending axially within said interior cavity, each radially spaced from said perimeter wall surface and concentric with the rotation axis of the impeller.

6. The rotary blood pump of claim 5 in which said cylindrical perimeter wall surface, said common circular arc and said plurality of open-ended cylinders are nested concentrically about the rotation axis of said impeller.

7. The rotary blood pump of claim 6 in which said plurality of open-ended cylinders comprises a radially innermost and a radially outermost open-ended cylinder.

8. The rotary blood pump of claim 7 in which said polyhedron bodies are positioned adjacent said cylindrical perimeter wall surface and said radially outermost open-ended cylinder is positioned radially inward from said polyhedron bodies.

9. The rotary blood pump of claim 8 in which each polyhedron body is integral with said cylindrical perimeter wall surface and with said radially outermost open-ended cylinder.

10. The rotary blood pump of claim 7 comprising an annular groove between said open-ended cylinders.

11. The rotary blood pump of claim 10 in which said annular groove between said open-ended cylinders is configured to obtain a ring permanent magnet.

12. The rotary blood pump of claim 10 in which an inner surface area of said radially outermost open-ended cylinder defines a radially outer boundary of said annular groove.

13. The rotary blood pump of claim 7 in which said innermost and outermost open-ended cylinders are of unequal axial length.

14. The rotary blood pump of claim 13 in which said radially innermost open-ended cylinder is axially longer than said outermost open-ended cylinder.

15. The rotary blood pump of claim 14 in which an open blood flow path extends through said impeller along the rotation axis thereof through said innermost open-ended cylinder.

16. The rotary blood pump of claim 1 in which each space between said spaced apart polyhedron bodies is configured to contain a permanent magnet.

17. The rotary blood pump of claim 1 in which a pair of said openings is formed in said predetermined surface areas of each selected polyhedron body.

18. The rotary blood pump of claim 1 in which each polyhedron body constitutes a selected polyhedron body and each surface area of each polyhedron body constitutes a predetermined surface area.

19. The rotary blood pump of claim 1 in which each of said openings comprises a bore closed at its inner end.

20. The rotary blood pump of claim 1 in which said selected polyhedron bodies comprises a diametrically opposed pair thereof.

21. The rotary blood pump of claim 1 in which each predetermined surface area comprises a planar polyhedron surface area adjacent the bottom of said impeller.

* * * * *